United States Patent
Dronov et al.

(10) Patent No.: US 10,758,741 B2
(45) Date of Patent: Sep. 1, 2020

(54) SYSTEM AND METHOD FOR SELECTIVE TREATMENT OF SKIN AND SUBCUTANEOUS FAT USING A SINGLE FREQUENCY DUAL MODE RADIO FREQUENCY ANTENNA DEVICE

(71) Applicant: Vasily Dronov, San Jose, CA (US)

(72) Inventors: Vasily Dronov, San Jose, CA (US); Erica Lee Elford, San Mateo, CA (US); Sylvia Helena Florez Marino, San Jose, CA (US)

(73) Assignee: Vasily Dronov, San Jose, CA (US)

( * ) Notice: Subject to any disclaimer, the term of this patent is extended or adjusted under 35 U.S.C. 154(b) by 402 days.

(21) Appl. No.: 15/564,383

(22) PCT Filed: Apr. 14, 2016

(86) PCT No.: PCT/US2016/027491
§ 371 (c)(1),
(2) Date: Oct. 4, 2017

(87) PCT Pub. No.: WO2016/168435
PCT Pub. Date: Oct. 20, 2016

(65) Prior Publication Data
US 2018/0133499 A1  May 17, 2018

Related U.S. Application Data

(60) Provisional application No. 62/147,489, filed on Apr. 14, 2015.

(51) Int. Cl.
*A61B 18/18* (2006.01)
*A61N 5/02* (2006.01)
(Continued)

(52) U.S. Cl.
CPC .......... *A61N 5/022* (2013.01); *A61B 18/1815* (2013.01); *A61N 1/403* (2013.01);
(Continued)

(58) Field of Classification Search
CPC ...... A61B 18/1815; A61B 2018/00029; A61B 2018/00464; A61B 2018/00642;
(Continued)

(56) References Cited

U.S. PATENT DOCUMENTS

| 4,121,592 A | 10/1978 | Whalley |
| 4,397,313 A | 8/1983 | Vaguine |

(Continued)

FOREIGN PATENT DOCUMENTS

| EP | 2022429 | 2/2009 |
| WO | 96/40369 | 12/1996 |

(Continued)

OTHER PUBLICATIONS

International Search Report and Written Opinion regarding corresponding PCT application No. PCT/US2016/027491, dated Jul. 21, 2016.

*Primary Examiner* — Thomas A Giuliani
*Assistant Examiner* — James A Cipriano
(74) *Attorney, Agent, or Firm* — Lewis & Reese, PLLC (57) ABSTRACT

A radio frequency system capable of selectively heating skin and subcutaneous fat tissues using a single frequency dual mode antenna device is disclosed. A detailed description and theory of operation of the antenna device are disclosed. The antenna device disclosed herein is capable of generating electric fields that are either mostly tangent, or mostly normal, to the skin surface, resulting in either predominantly heating skin or predominantly heating fat. The method for treating skin and subcutaneous fat tissues using such system is also disclosed.

31 Claims, 7 Drawing Sheets

(51) Int. Cl.
*A61N 1/40* (2006.01)
*A61N 5/06* (2006.01)
*A61B 18/00* (2006.01)
*A61N 5/00* (2006.01)

(52) U.S. Cl.
CPC .. *A61N 5/0616* (2013.01); *A61B 2018/00029* (2013.01); *A61B 2018/00464* (2013.01); *A61B 2018/00642* (2013.01); *A61B 2018/00678* (2013.01); *A61B 2018/00708* (2013.01); *A61B 2018/00714* (2013.01); *A61B 2018/00779* (2013.01); *A61B 2018/00797* (2013.01); *A61B 2018/00863* (2013.01); *A61B 2018/00994* (2013.01); *A61N 5/0625* (2013.01); *A61N 2005/007* (2013.01); *A61N 2005/0652* (2013.01); *A61N 2005/0663* (2013.01)

(58) Field of Classification Search
CPC ........... A61B 2018/00678; A61B 2018/00708; A61B 2018/00714; A61B 2018/00779; A61B 2018/00797; A61B 2018/00863; A61B 2018/00994; A61B 2018/00452–0047; A61N 1/403; A61N 5/02; A61N 5/022; A61N 5/025; A61N 5/0616; A61N 5/0625; A61N 2005/007; A61N 2005/0652; A61N 2005/0663
See application file for complete search history.

(56) References Cited

U.S. PATENT DOCUMENTS

| | | | |
|---|---|---|---|
| 5,010,897 A | | 4/1991 | Leveen |
| 5,099,756 A | | 3/1992 | Franconi et al. |
| 5,101,836 A | | 4/1992 | Lee |
| 5,246,438 A | | 9/1993 | Langberg |
| 5,503,150 A | | 4/1996 | Evans |
| 5,549,639 A | * | 8/1996 | Ross ................. A61N 5/02 607/101 |
| 5,769,879 A | * | 6/1998 | Richards ............ A61N 5/04 607/101 |
| 5,931,807 A | | 8/1999 | McClure et al. |
| 6,208,903 B1 | | 3/2001 | Richards et al. |
| 6,387,380 B1 | | 5/2002 | Knowlton |
| 6,413,255 B1 | | 7/2002 | Stern |
| 6,527,768 B2 | | 3/2003 | Berube |
| 6,749,624 B2 | | 6/2004 | Knowlton |
| 6,920,883 B2 | | 7/2005 | Bessette et al. |
| 8,035,570 B2 | | 10/2011 | Prakash et al. |
| 8,172,835 B2 | | 5/2012 | Leyh et al. |
| 8,211,097 B2 | | 7/2012 | Leyh |
| 8,287,579 B2 | | 10/2012 | Nimitz |
| 8,343,145 B2 | | 1/2013 | Brannan |
| 8,454,591 B2 | | 6/2013 | Leyh et al. |
| 8,469,951 B2 | | 6/2013 | Ben-Haim et al. |
| 8,500,729 B2 | | 8/2013 | Bystryak et al. |
| 8,548,599 B2 | | 10/2013 | Zarsky et al. |
| 8,676,338 B2 | | 3/2014 | Levinson |
| 8,853,600 B2 | | 10/2014 | Spertell |
| 8,974,449 B2 | | 3/2015 | Brannan |
| 2002/0049483 A1 | | 4/2002 | Knowlton |
| 2004/0206365 A1 | | 10/2004 | Knowlton |
| 2004/0210214 A1 | | 10/2004 | Knowlton |
| 2005/0251117 A1 | | 11/2005 | Anderson et al. |
| 2006/0020312 A1 | | 1/2006 | Eggers et al. |
| 2006/0122508 A1 | | 6/2006 | Slayton et al. |
| 2006/0265034 A1 | | 11/2006 | Aknine et al. |
| 2006/0271028 A1 | | 11/2006 | Altshuler et al. |
| 2007/0060989 A1 | | 3/2007 | Deem et al. |
| 2007/0078502 A1 | | 4/2007 | Weber et al. |
| 2007/0083247 A1 | | 4/2007 | Wyeth et al. |
| 2007/0088413 A1 | | 4/2007 | Weber et al. |
| 2007/0282318 A1 | | 12/2007 | Spooner et al. |
| 2008/0097559 A1 | | 4/2008 | Eggers et al. |
| 2008/0269851 A1 | * | 10/2008 | Deem ................. A61B 18/18 607/101 |
| 2009/0171341 A1 | | 7/2009 | Pope et al. |
| 2010/0010480 A1 | | 1/2010 | Mehta et al. |
| 2010/0030210 A1 | | 2/2010 | Paulus |
| 2010/0114086 A1 | | 5/2010 | Deem et al. |
| 2010/0152824 A1 | | 6/2010 | Allison |
| 2010/0198064 A1 | * | 8/2010 | Perl .................... A61B 8/546 600/439 |
| 2010/0211059 A1 | | 8/2010 | Deem et al. |
| 2010/0211060 A1 | * | 8/2010 | Baron ................. A61B 18/14 606/33 |
| 2011/0066145 A1 | | 3/2011 | Epstein et al. |
| 2012/0016356 A1 | | 1/2012 | Beale et al. |
| 2013/0238062 A1 | | 9/2013 | Ron Edoute et al. |
| 2016/0346031 A1 | * | 12/2016 | Anand ................ A61N 7/02 |

FOREIGN PATENT DOCUMENTS

| | | |
|---|---|---|
| WO | 2003/103768 | 12/2003 |
| WO | 2009/126117 | 10/2009 |
| WO | 2013/019785 | 2/2013 |
| WO | 2014/182822 | 11/2014 |

* cited by examiner

SYSTEM AND METHOD FOR SELECTIVE TREATMENT OF SKIN AND SUBCUTANEOUS FAT USING A SINGLE FREQUENCY DUAL MODE RADIO FREQUENCY ANTENNA DEVICE

FIELD OF THE INVENTION

This invention is generally related to a radio frequency (RF) energy delivery device for treating skin and subcutaneous fat tissues.

BACKGROUND

The skin is the largest organ system in the body, providing a protective barrier between the internal and external environment. The skin is made up of connective tissue with a variety of cell types. With natural aging and ultraviolet light exposure there is a gradual thinning and decrease in structural integrity of the skin. Fibroblasts, the cells responsible for connective tissue production, exhibit enhanced proliferation and protein synthesis following heat stimulation. At the protein level, temperature elevation in the connective tissue of skin produces an effect on matrix proteins, such as collagen. Immediate collagen contraction is followed by deposition and remodeling. Therefore, energy delivery to the skin will promotes improved elasticity, dermal tightening and overall skin rejuvenation.

Light and heat exposure to the skin can also be used to treat acne and resolve the associated inflammatory response. Bacteria and sebum are two components of acne. Sebum, the oily or waxy secretion for lubrication and waterproofing the skin, accumulates during acne. Sebum also serves as a food source for bacteria thereby promoting bacterial growth and subsequent inflammation. During metabolism, bacteria produce porphyrins. Upon exposure to light of blue wavelengths, the porphryins become activated and cause bacterial death, ultimately helping clear the acne. Additionally, heat can have a dual function for acne. Heat can kill bacteria and help accelerate the resolution of the acne lesion. Together light and heat exposure to the skin can help treat and resolve acne lesions on the skin.

Subcutaneous fat is a widely distributed tissue layer beneath the skin that provides protection, thermoregulation, and an energy reserve. Subcutaneous fat is comprised of fat cells, which store triglycerides, and are separated into lobules by an organized by a network of fibrous septae. Composed from connective tissue, the fibrous septae occur parallel, perpendicular, or oblique to the skin surface.

Alterations in the subcutaneous tissue can result in skin surface topology changes, commonly called cellulite. Compared to normal tissue, cellulite may reflect differences in fat tissue biochemistry, or connective tissue structure. Disruptions in fat cell metabolism or fibrous septae orientation may result in focal herniation of fat into the skin producing surface distensions. Furthermore, skin damage or changes in elasticity are also associated with cellulite. Therefore the development of a novel, non-invasive method for fat reduction with simultaneous dermal tightening is needed.

Cellulite has a complex etiology and consequentially requires a multifaceted therapeutic approach. At the tissue level, temperature elevation improves capillary and lymphatic microcirculation. At the cellular level, temperature elevation influences fat cells and fibroblasts. The heating of fat cells induces metabolic alterations, membrane permeability for lipid release, apoptosis, and necrosis. Increased connective tissue production by heat-induced fibroblasts prohibit fat protrusion into the skin, and alleviate alterations in fibrous septae orientation. Therefore selective heating of skin and fat tissues will provide a customizable and effective remedy for subcutaneous tissue alterations.

In non-cellulite related applications such as skin rejuvenation and acne treatment, the skin is the primary target for energy delivery. Nonetheless, the ability to selectively heat both skin and fat may be advantageous. By either preheating subcutaneous fat prior to skin treatment, or by simultaneously delivering energy to the skin and subcutaneous fat, an effect can be achieved where deeper dermal layers are heated to higher temperatures as compared to the epidermis. Thus, an inverse temperature gradient in the skin can be achieved. Since nerve fibers are denser in the surface layers of the skin, a lesser amount of discomfort can be expected for treatments utilizing tissue-specific energy delivery.

Common technologies to deliver energy into the skin and fat include: laser and light emitting diode (LED) light, ultrasound and radio frequency (RF). RF heating is a preferred method of energy delivery when either a large volume of tissue is being treated and uniform energy absorption is sought, or greater penetration depths are required.

RF systems intended to treat skin and subcutaneous fat have been known in the art for a number of years. The vast majority of these systems use an RF energy source operating in the range of several hundreds of kilohertz (kHz) to several megahertz (MHz). These systems utilize either a small treatment electrode located on the handpiece coupled with a large return electrode attached to the patient, or a system of multiple small electrodes located on the handpiece.

Complications associated with monopolar RF systems utilizing a return electrode include the need for impedance matching (see U.S. Patent Application Publication No. 20070083247) and impedance sensing hardware (see U.S. Patent Application Publication No. 20070078502). Yet another complication occurring with all low frequency RF systems is the unwanted heating of the treatment electrode edges created by increased current density, or the so called "edge effect" phenomenon. To mitigate this effect, a complex cryogenic cooling system is frequently introduced (see U.S. Patent Application Publication No. 20020049483 and U.S. Pat. No. 6,413,255).

To selectively target a particular tissue layer some systems employ a multi-electrode energy delivery system that claims to influence the depth of energy delivery, although not the tissue type (see U.S. Patent Application Publication No. 20070088413). Other systems, (as described in U.S. Patent Publication No. 20100211060) purportedly selectively treat subcutaneous fat but not the skin. Yet other systems, purportedly target multiple tissue layers (see U.S. Patent Application Publication US 20100211059). However, such systems rely on the wide band RF energy source, making the overall apparatus complex. Also, it is also unclear if such a device is capable of selectively heating a fat layer that is several centimeters thick.

Thus, RF systems having the following improvements are needed:

(i) the capability to selectively heat skin and/or subcutaneous fat tissues, thereby providing new treatment options.

(ii) the capability to use a single frequency or a narrow band RF source, reducing the overall complexity and cost of the system.

(iii) uniform energy delivery by using an RF antenna based system operating near to, or in the microwave frequency range to eliminate the electrode edge effects that occur in the majority of the existing RF systems. Uniform energy delivery removes the requirement for a complex cryogenic cooling system for the treatment electrode and allows for accurate skin surface temperature measurements. Furthermore, uniform energy yields increased patient comfort, decreased procedural times and maintenance of therapeutic temperature levels; thereby providing improved clinical outcomes. As used herein, the term microwave is as defined in the seventh edition of IEEE 100, The Authoritative Dictionary of IEEE Standards Terms, "pertaining to the portion of the radio frequency spectrum above 1 GHz."

(iv) elimination of the return electrode.

SUMMARY

The present disclosure is directed to a radio frequency (RF) system using a single frequency dual mode antenna capable of selectively heating skin and subcutaneous fat tissues. In one embodiment, the RF system is comprised of a console, a handpiece, and an interconnection module. To administer treatment, the handpiece is placed on the patient treatment area and energy delivery is configured via a graphical user interface (GUI). The dual mode antenna will selectively heat the skin and subcutaneous fat. In another embodiment, the system includes a compact, approximately 1 cm diameter antenna device and a low power RF energy source. The treatment will be self-administered by a handheld home use device. In this case, the antenna can operate as a single mode device to selectively heat the skin, or as a dual mode device to mainly heat the skin but also heat the fat layer if there is a need to target deeper layers of the dermis.

At the center of the disclosed invention, the design and the theory of operation of a dual mode antenna device are provided. This dual mode antenna device is capable of generating electric fields that are either mostly tangent, or mostly normal to the skin surface, resulting in either predominantly heating skin or predominantly heating fat. A system equipped with this antenna device can be used either as a skin rejuvenation system or body contouring system, since both applications benefit from the ability to selectively deliver RF energy to a specific tissue type.

Additionally disclosed herein are the methods for: heating the skin and subcutaneous fat tissues through RF energy delivery, simultaneous energy delivery to skin and fat with the desired power ratios, and using the system to determine the skin surface and subcutaneous fat temperatures.

Further advantages of the disclosed invention will become evident through examination of the detailed description.

BRIEF DESCRIPTION OF THE DRAWINGS

The accompanying drawings illustrate the various embodiments of the principles described herein. The illustrated embodiments are merely examples and do not limit the scope of the disclosure.

DESCRIPTION

System Description.

Figure 1:
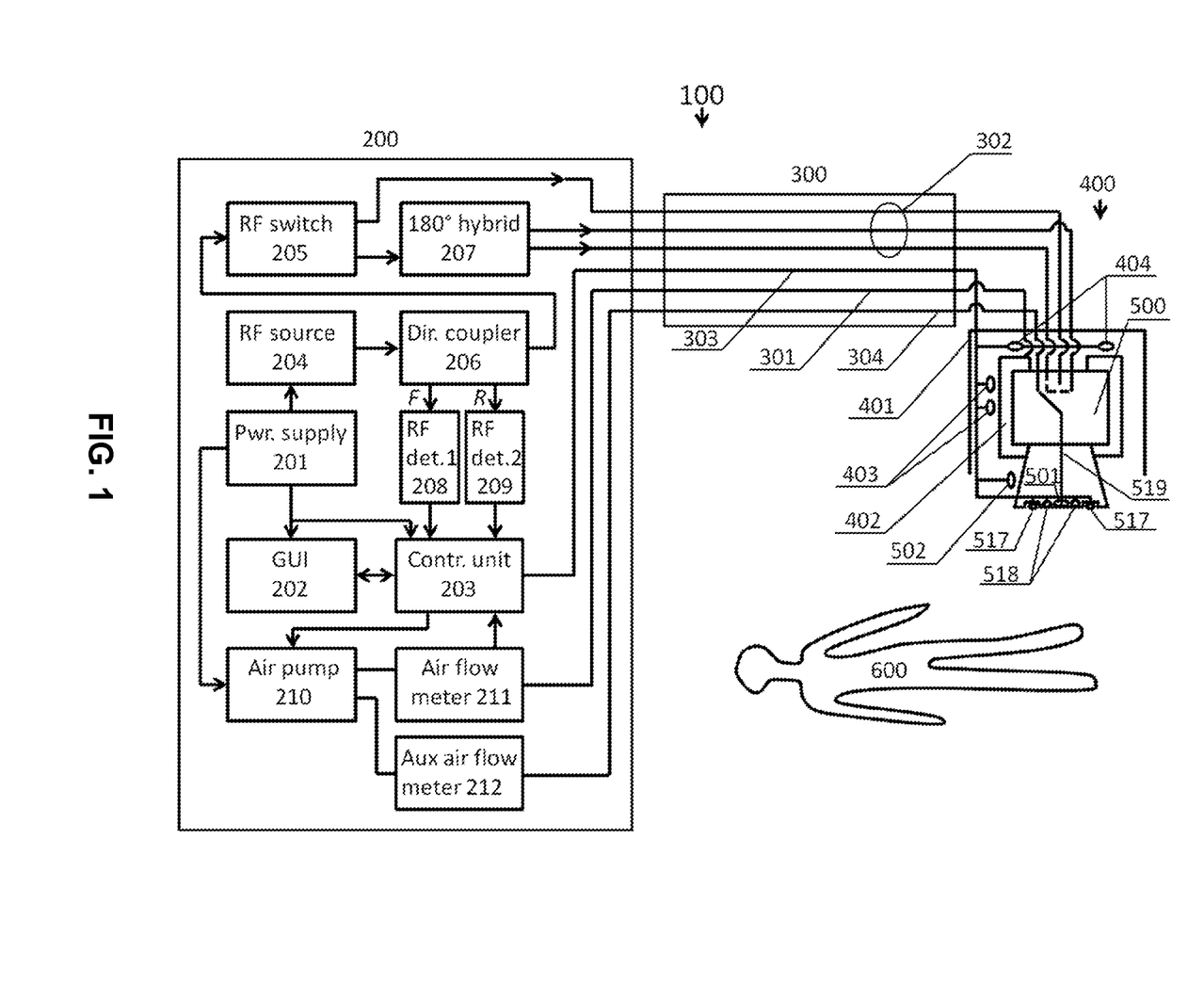
FIG. 1 shows a diagram for the disclosed system.

FIG. 1 shows a diagram of a system for providing thermal therapy to a patient. The system 100 includes three main components: a console 200, a handpiece 400, and a interconnection module 300. The console 200 includes a power supply 201, a graphical user interface (GUI) 202, a controller unit 203, a narrow band, variable power level RF source 204, an RF power switch 205, a directional coupler 206, a 180° hybrid power splitter 207, RF detector 1 208, RF detector 2 209, an air pump 210, and an air flow meter 211. An auxiliary air flow meter 212 can be added to monitor air flow to the center of the treated skin area, if more precise skin temperature control mechanism is desired.

The controller unit typically includes one or more processors programmed to execute duties assigned to the controller unit. For example, the controller may include one or more central processing units (CPU) or graphics processing units (GPU) and supporting architecture, as is known in the art. Examples of suitable processors include INTEL i5 and i7 processors, among others. The processors can be configured to load instructions from memory (for example read only memory (ROM) or random access memory (RAM)). The processors are configured to interact with and control the components of the console 200 using one or more application program interfaces (API).

The console may be integrated into a single component, as depicted in FIG. 1. Alternatively, the console may comprise multiple modular components. For example, the power supply may be contained within a different module than the GUI. For simplicity, such modular components are collectively referred to herein as a console.

The handpiece 400 includes an enclosure 401, an antenna device 500, an air duct 402, a plurality of control switches 403, a plurality of force sensors 404, a plurality of temperature sensors 501, 502 and 517 embedded into the antenna device 500, and a plurality of optional light sources 518. The handpiece 400 is placed onto the patient's body 600 when administering treatment. The interconnection module 300 includes an air line 301, an auxiliary air line 304, a plurality of coaxial power cables 302, one or more electrical cables 303 linking the control switches 403, force sensors 404, and temperature sensors 501, 502 and 517 in the handpiece 400 with the controller unit 203 in the console 200.

Figure 2A:
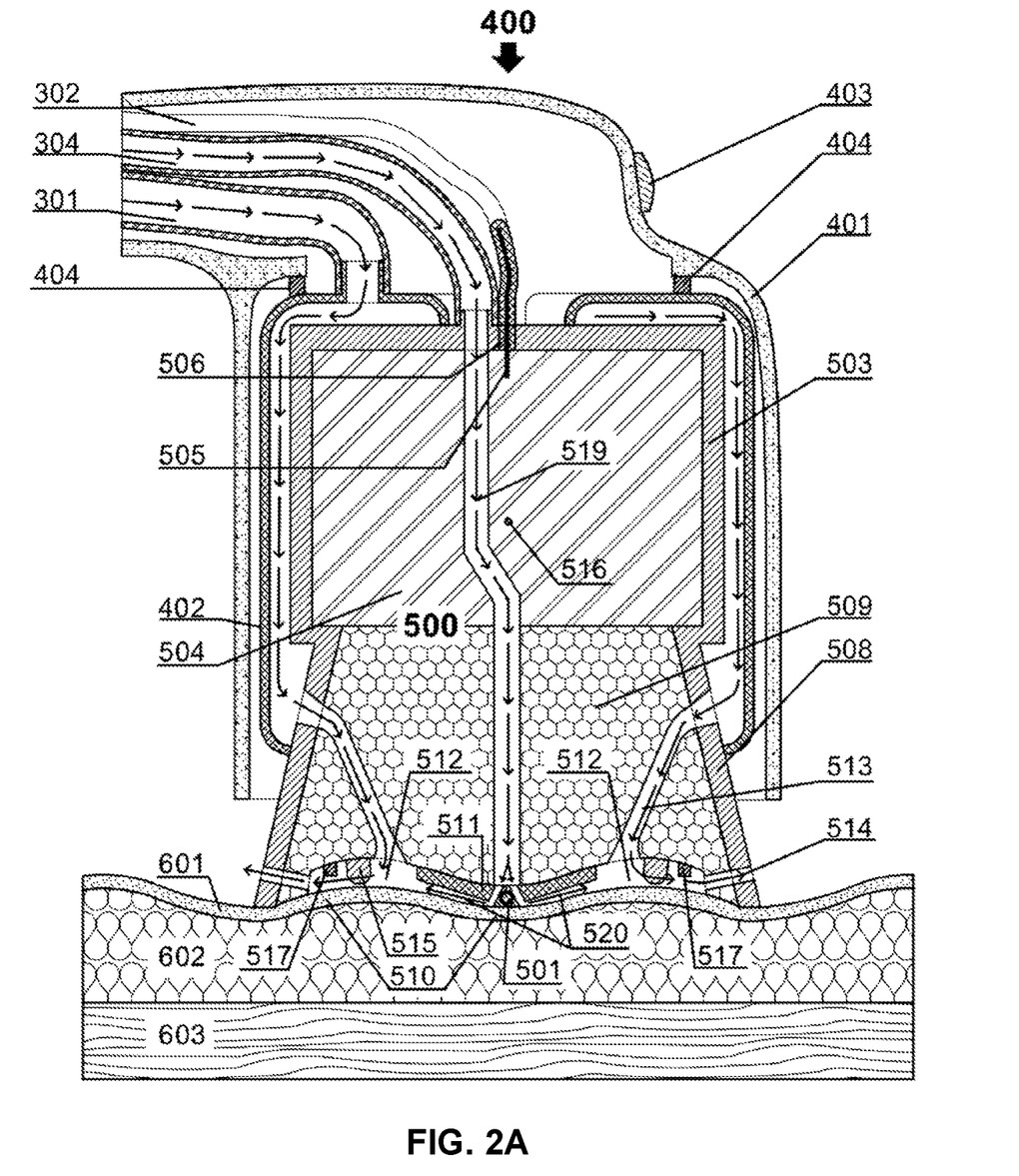
FIG. 2A shows a cross-sectional view of an exemplary embodiment of an antenna device and a handpiece.
Figure 2B:
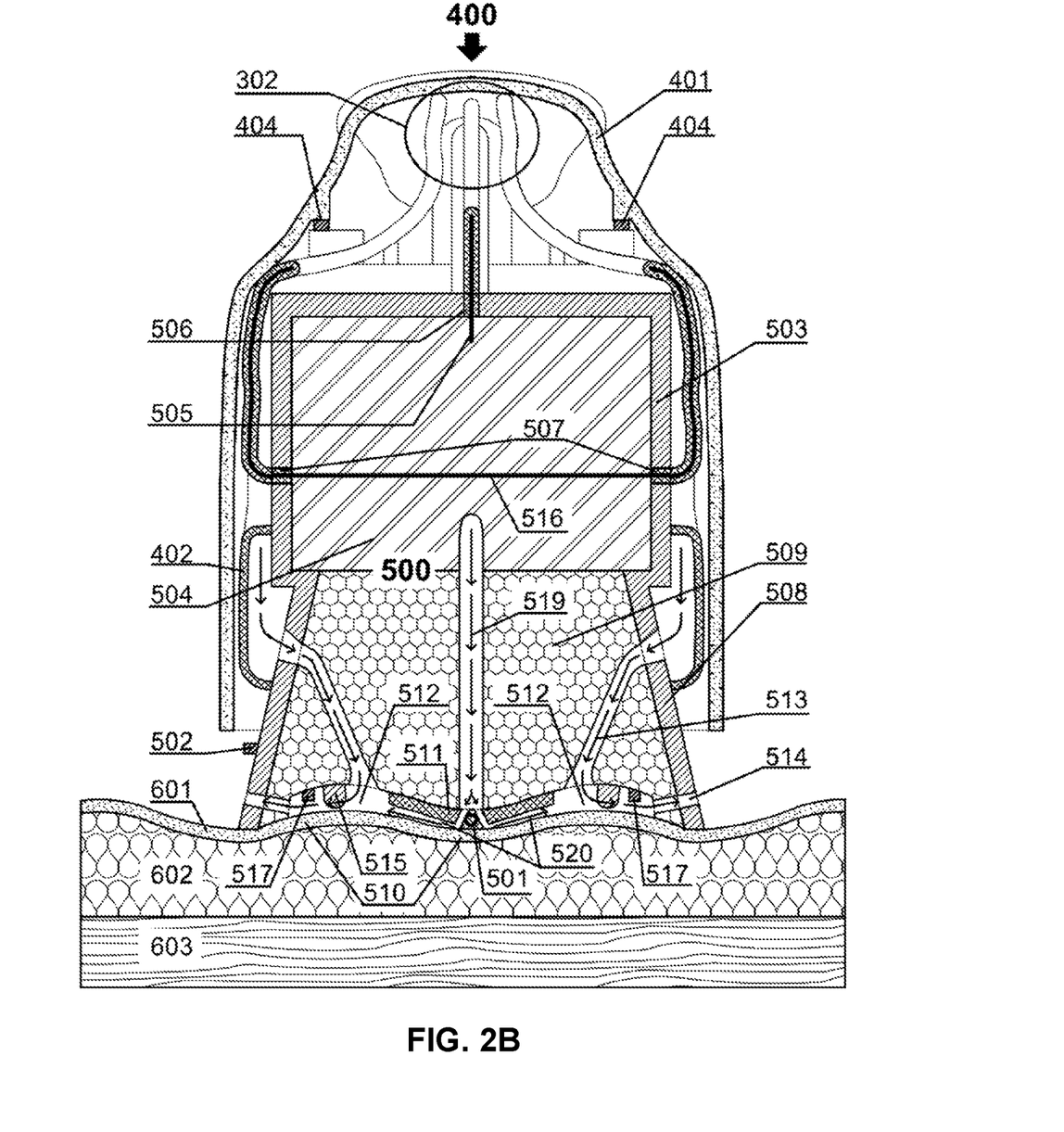
FIG. 2B shows an additional cross-sectional view of an exemplary embodiment of an antenna device and a handpiece.

FIGS. 2A and 2B show one embodiment of the antenna device 500 housed inside one embodiment of the handpiece 400. FIG. 2A shows a cross-sectional view of the handpiece 400 in the plane comprising the axis of the antenna device and normal to the transverse electric (TE) mode feed 516. FIG. 2B shows a cross-sectional view of the handpiece 400 in the plane comprising the axis of the antenna device and the TE mode feed 516.

The antenna device 500 comprises a main metallic resonator tank 503 filled with dielectric material 504 and containing a transverse magnetic (TM) mode feed 505 with a feed insulator 506 and a TE mode feed 516 with feed insulators 507; a metallic horn 508 attached to the main tank 503 and filled with dielectric material 509, and having the bottom surface curvature 510 optimized to reduce unintended heating of skin 601 while treating subcutaneous fat tissue 602. The dielectric material can be any dielectric material, but according to some embodiments is a thermoplastic material, for example, a moldable thermoplastic. A particular example of a suitable dielectric is PREPERMA® L900HF, available from Premix OY, Rajamäki, Finland. The dielectric constant may be about 9.0, for example. But it is within the ability of a skilled artisan to select an appropriate dielectric material.

The handpiece further includes a temperature sensor A housing 511 having a temperature sensor A 501 embedded into the temperature sensor A housing 511; a second temperature sensor B 502; a ring shaped airduct 512 embedded into the dielectric material 509 in the bottom part of the antenna device 500; a plurality of temperature sensors C 517 located within the airduct 512; a number of small air channels 513 embedded into the dielectric material 509 that link the large airduct 402 with the ring shaped airduct 512; a plurality of vent holes 514 linking the ring shaped airduct 512 with ambient air surrounding the antenna device 500; a plurality of standoffs 515 located inside the ring shaped airduct 512 that protrude toward the skin 601. The auxiliary airduct 519 and vent holes 520 can be added if a more precise skin temperature control mechanism is desired. The auxiliary airduct 519 could, for instance, be routed through the center axis of the antenna device.

The plurality of light sources 518 are used with antenna embodiments intended for acne treatment and are generally comprised of one or multiple LEDs or laser diodes which predominantly emit light with a blue or violet spectrum.

Energy Absorption Rate in Skin and Subcutaneous Fat for Electric Fields Tangent and Normal to the Skin Surface.

In the following discussion, the physical mechanism behind selective heating of skin and subcutaneous fat via RF will be explained. It is assumed that the skin conforms to the antenna device surface near antenna's axis where electric fields in the antenna are the strongest. It is also assumed there is a clear boundary between the skin, the fat, and the muscle tissue layers. Two cases will be considered: in the first case the incident electric field induced by the antenna device at the skin surface is predominantly tangent with the skin surface; in the second case the field is normal to the skin surface.

In non-magnetic materials the amount of power Q absorbed per unit volume of the material is calculated as $\frac{1}{2} \sigma_{eff}|E|^2$, where $\sigma_{eff}=\sigma_c+2\pi f\varepsilon''$, $\sigma_c$ is material conductivity, f is frequency, $\varepsilon''$ is the imaginary part of material's permittivity and $|E|$ is the magnitude of electric field. For frequencies in the hundreds of MHz range or greater, the losses in biological tissues are strongly dominated by the tissue permittivity, thus $$Q=\tfrac{1}{2}\sigma_{eff}|E|^2=\pi f\varepsilon''|E|^2 \quad (1).$$

At the skin and fat layer interface the tangential component of the electric field has to be same in both tissues, i.e., $$E_{skin}^{tan}=E_{fat}^{tan} \quad (2),$$

while the normal components of the electric field are related through tissue permittivities as $$\varepsilon_{skin}E_{skin}^{norm}=\varepsilon_{fat}E_{fat}^{norm} \quad (3).$$

Since the main objective is to determine how different the energy absorption rates are in the two tissue layers depending on the configuration of the antenna device, two quantities, $\eta_{tan}$ and $\eta_{norm}$, which relate to energy absorption efficacy for a given orientation of electric field, are introduced:

$$\eta_{tan}=Q_{skin}/Q_{fat} \quad (4A),$$

$$\eta_{norm}=Q_{fat}/Q_{skin} \quad (4B).$$

Using EQs. (1)-(4) one can now calculate $\eta_{norm}$ and $\eta_{norm}$ for the cases where the electric field induced by the antenna device in the two tissue layers is either predominantly tangent or normal to the skin surface. For the case of predominantly tangent field, one will arrive at the following result:

$$\eta_{tan}=Q_{skin}/Q_{fat}=\varepsilon_{skin}''/\varepsilon_{fat}'' \quad (5).$$

For the case of predominantly normal field, one will arrive at the following result:

$$\eta_{norm}=Q_{fat}/Q_{skin}=(\varepsilon fat''|E_{fat}|^2)/(\varepsilon_{skin}''|E_{skin}|^2)=(\varepsilon_{fat}''|\varepsilon_{skin}|^2)/(\varepsilon_{skin}''|\varepsilon_{fat}|^2) \quad (6).$$

For the antenna device to function optimally, $\eta_{tan}$ and $\eta_{norm}$ should have values greater than unity. The farther $\eta$ is from unity for each of the electric field orientations, the higher the attainable efficacy of the antenna device.

Figure 3:
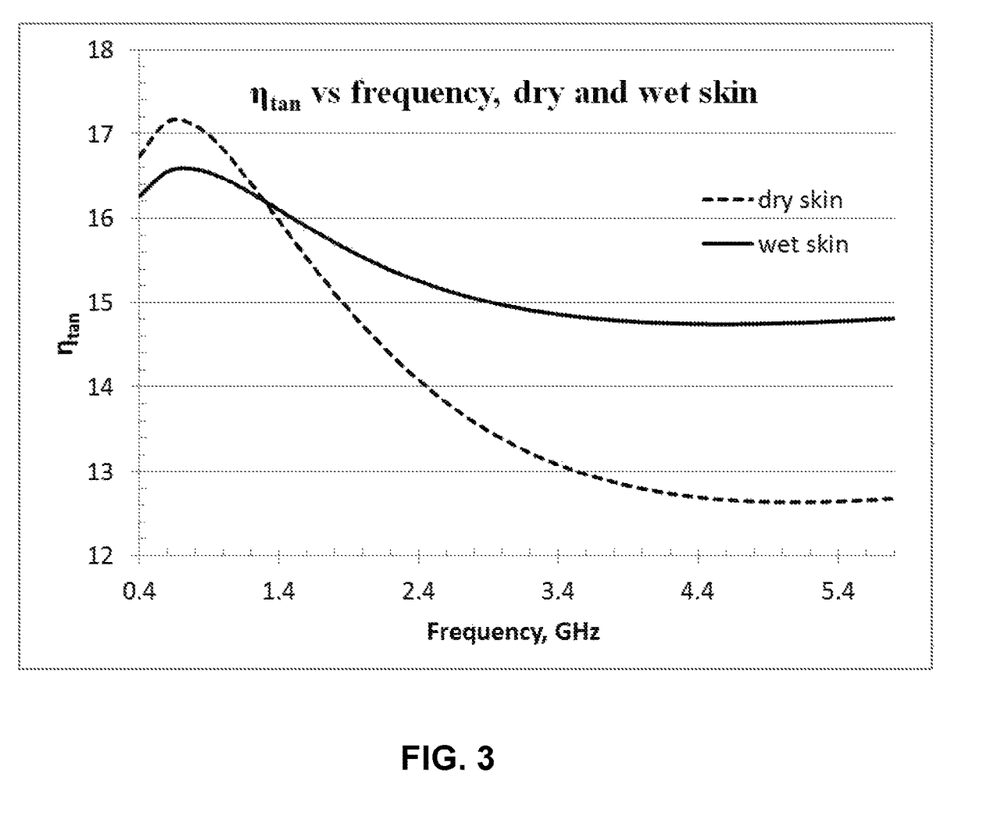
FIG. 3 shows a plot of the energy absorption efficacy versus the frequency for the case of tangent electric field.
Figure 4:
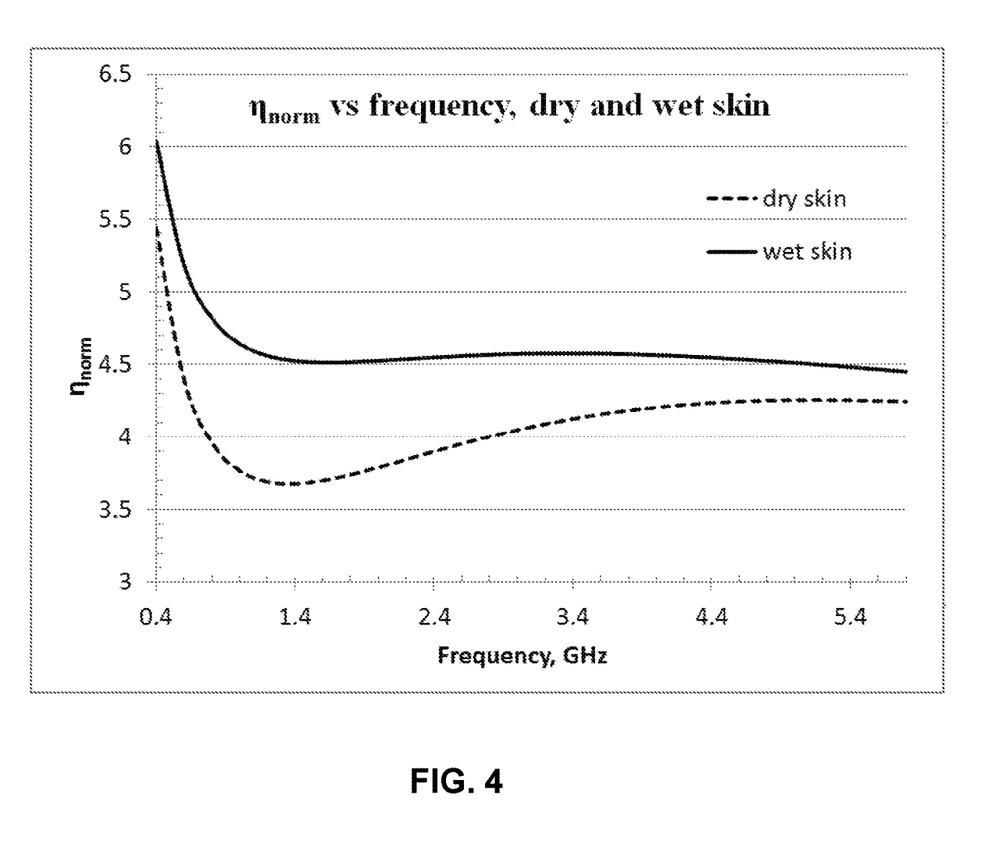
FIG. 4 shows a plot of the energy absorption efficacy versus the frequency for the case of normal electric field.

Referring to FIG. 3 and FIG. 4, $\eta_{tan}$ and $\eta_{norm}$ as plotted as a function of frequency for skin and fat models based on the widely cited tissue measurement results (see S. Gabriel, et al. titled "The dielectric properties of biological tissues"). FIG. 3 demonstrates that for the tangent field the value of $\eta_{tan}$ is high irrespective of frequency or wetness of the skin. In the case of normal electric field (FIG. 4) $\eta_{norm}$ reaches notably higher values for wet skin which suggests that wetting the patient's skin during treatment would improve overall efficacy of the antenna device. One additional observation related to the data in FIG. 4 is that the value of $\eta_{norm}$ becomes greater at lower frequencies. While building a compact antenna device capable of operation at very low frequencies may not be feasible, the data in FIG. 4 should be considered when choosing the optimal frequency to deliver energy into tissue.

It is important to note that the muscle layer 603 located below the fat layer 602 will also experience some heating when the treated area is exposed to either the tangent or normal electric field. However, due to muscle's very high permittivity value and the cooling effect coming from the blood perfusion present in the muscle tissue, such heating is generally very small. This statement has been confirmed through simulations.

Dual Mode Antenna Device Based on the Open Ended Axisymmetric Cavity.

Choosing an axisymmetrical cavity as a basis for the antenna design is mainly driven by the following factors: (i) circular symmetry of an axisymmetrical cavity allows generation of electric fields concentrated in a circular pattern near the cavity's main axis; (ii) when the height of a cylindrical cavity is approximately equal to its diameter, the cavity can supports two distinct modes—a transverse electric (TE) mode TE111 and a transverse magnetic (TM) mode TM010—with both modes having identical resonant frequency. TE111 and TM010 are the lowest frequency modes that can exist in a cylindrical cavity, and thus using these two modes minimized the dimensions of the antenna device. It has been determined via numerical modeling that a more general type of axisymmetrical cavity structure like the one utilized by the antenna device 500 disclosed herein, can also support similar modes behaving similarly to TE111 and TM010.

The ability of the disclosed herein antenna device to selectively heat multiple tissue types using a single frequency energy source is advantageous since a single frequency or, in more practical terms, a narrow band RF power source can be built to be more compact, energy efficient and less costly when compared to a wide band RF power source. Simultaneously, it is acceptable to use such an RF source outside of its nominal frequency range when operating it at much lower power levels, for instance, when estimating the fat layer thickness. In the latter case the RF source does not need to have either high efficiency, or output maximally specified amount of power.

In a cross-sectional plane normal to the cylindrical cavity's main axis, the electric field of TE111 mode is tangent to the cross-sectional plane, while the electric field of TM010 mode is normal to the cross-sectional plane. Since the two modes are decoupled from each other, RF energy can be channeled into either of the individual or both modes simultaneously with any desired energy ratio between the two.

In a situation where one end wall of the resonant cavity is removed and the open end of the cavity is pressed against the patient's skin, the skin and underlying tissues (mostly muscle) act as a cavity end wall. Muscle tissue is characterized by high permittivity similar to that of water which allows displacement currents to flow below the resonant cavity with relative ease, thus performing a function similar to that of a metallic cavity end wall.

Figure 5:
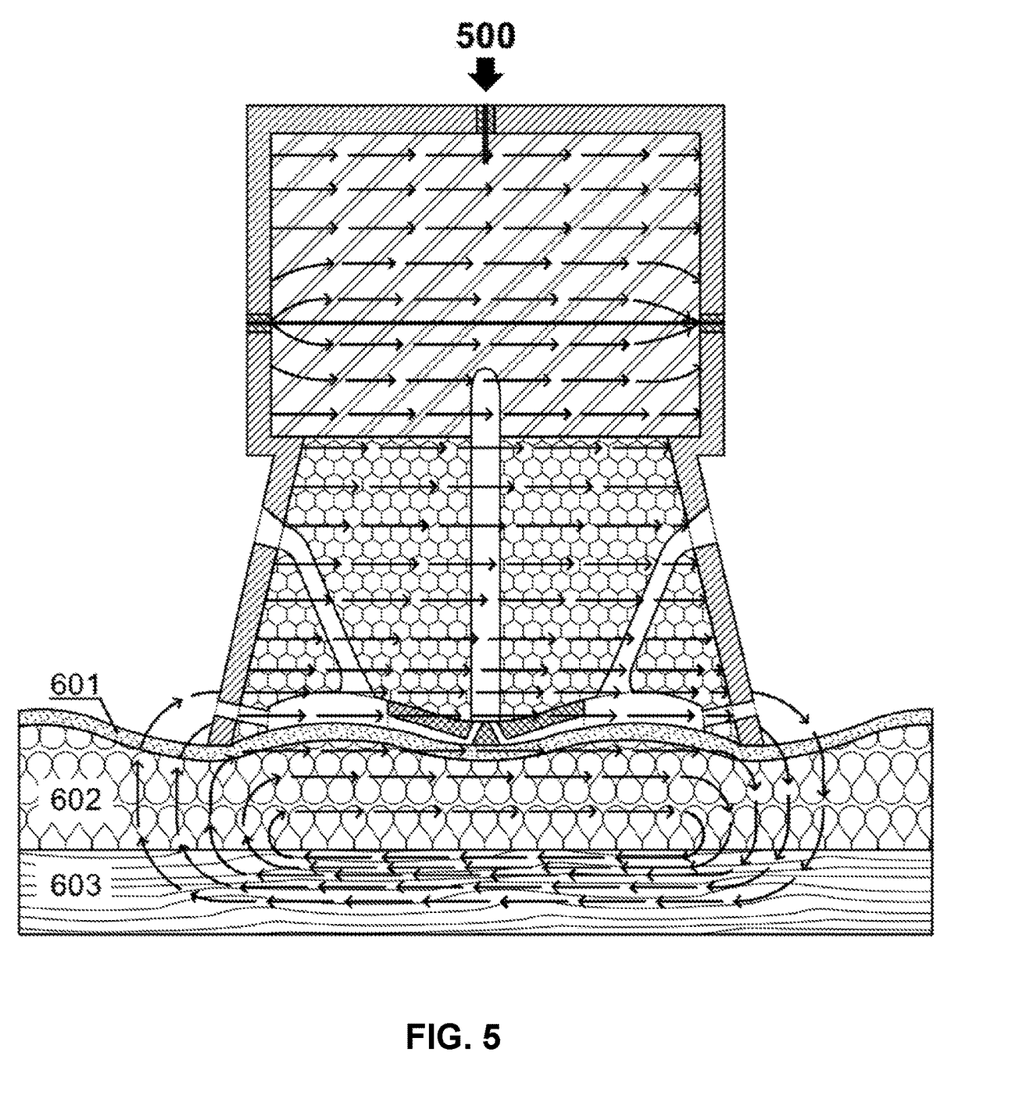
FIG. 5 qualitatively illustrates the electric field distribution for quasi TE111 mode.

FIG. 5 shows approximate distribution of electric fields inside the antenna device 500 pressed against patient's skin 601, with quasi, or TE111-like mode excited inside the cavity. What is implied here by quasi TE111 mode is the lowest frequency mode that exists in the cavity-patient configuration shown in FIG. 5 for which the fields inside the cavity are distributed qualitatively similar to those of the TE111 mode in a cylindrical cavity. The electric field is substantially tangential to the skin surface inside the cavity. By substantially tangential, it is meant that, on average, the electric field E within the treatment area of the skin at the skin surface has the magnitude of the tangential component to the skin $E_{tan}$ exceed the magnitude of the normal component $E_{norm}$. If expressed in the form of a surface integral over the treated skin surface area S, the definition of substantially tangential electric field equates to $\oint_S(|E_{tan}|-|E_{norm}|)dS>0$. According to simulation results, the electric field intensity is also the strongest near the main axis of the cavity.

One important property of the TE111-like mode is that the resonant frequency of the antenna loaded with tissue decreases slightly as the thickness of the fat layer increases. Thus performing a low power frequency sweep of the loaded antenna device using TE111-like mode can assist with estimating the fat layer thickness. In turn, the fat thickness measurement allows one to calculate the optimal amount of energy needed to heat the fat to a desired temperature. It should be noted that for the antenna device 500 embodiment disclosed herein, the effective bandwidth of the antenna when using TE111-like mode is rather wide, thus the antenna's ability to accept power from the RF source is maintained as the fat layer thickness varies.

Figure 6:
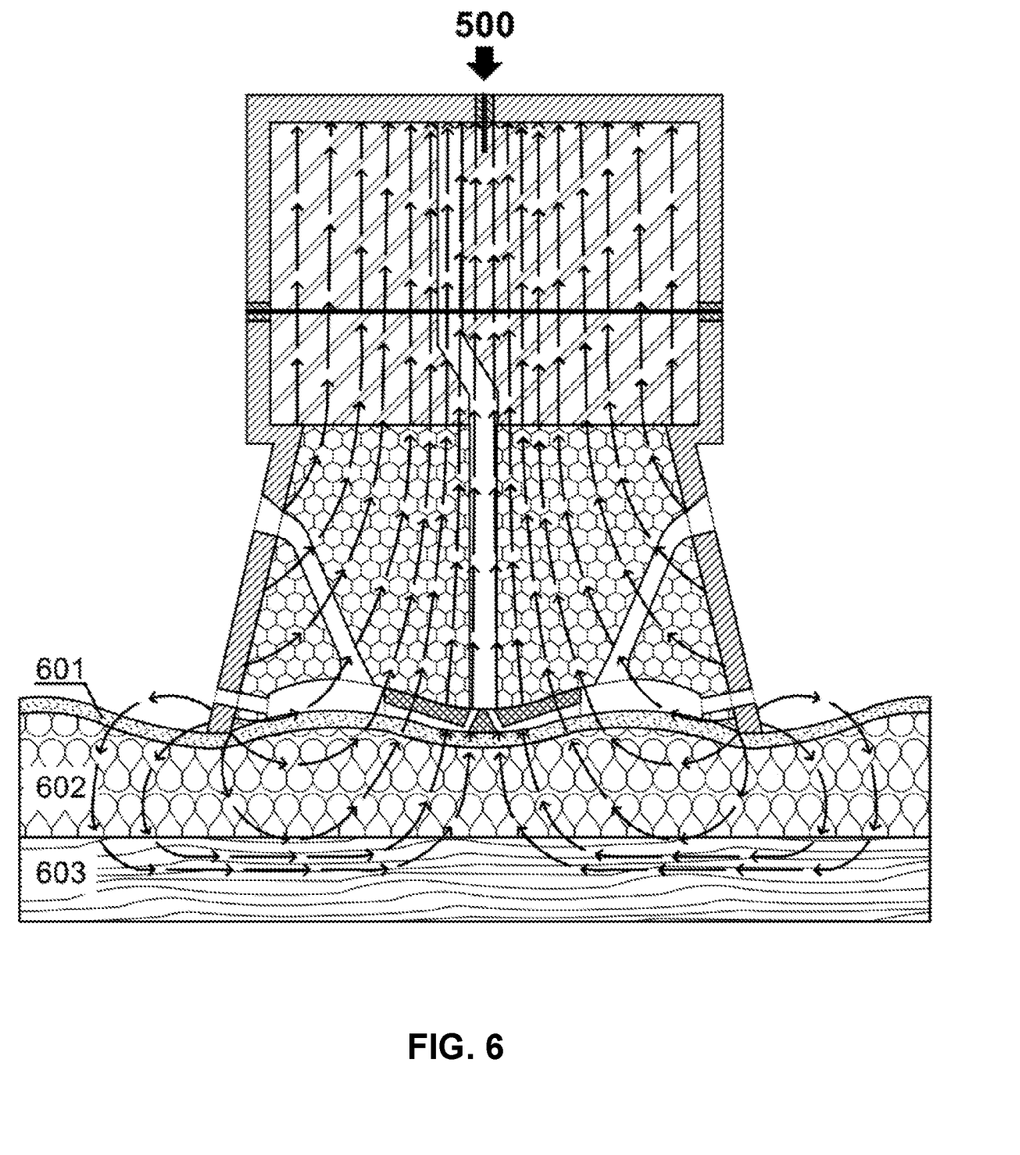
FIG. 6 qualitatively illustrates the electric field distribution for quasi TM010 mode.

FIG. 6 shows the approximate distribution of electric fields inside the same resonant cavity pressed against the patient's skin, with a quasi, or TM010-like mode excited inside the cavity. As before, what is implied here by quasi TM010 mode is the lowest frequency mode that exists in the cavity-skin configuration shown in FIG. 6 for which the fields inside the cavity are distributed qualitatively similar to those of the TM010 mode in a cylindrical cavity. One can see that the electric field is substantially normal to the skin surface near the axis of the cavity and also most intense near the axis. By substantially normal, it is meant that, on average, the electric field E within the treatment area of the skin at the skin surface has the magnitude of the normal component to the skin $E_{norm}$ exceed the magnitude of the tangential component $E_{tan}$. If expressed in the form of a surface integral over the treated skin surface area S, the definition of substantially normal electric field equates to $\oint_S(|E_{norm}|-|E_{tan}|)dS>0$. Similar to the TM010 mode, the quasi TM010 mode's resonant frequency appears to be mostly unaffected by the cavity's height. This allows adjustment of the cavity height in such way that the resonant frequencies for the quasi TE111 and quasi TM010 modes are the same for the nominal fat layer thickness.

System Operation and Use.

Referring to FIG. 1, the controller unit 203 controls and monitors operation of all other modules in the system 100 to ensure the system's safe operation. The graphical user interface (GUI) 202 in the console 200 is used to configure the system 100, display treatment status and generate alerts.

The RF source with variable power level 204 powered by the power supply 201 and controlled by the controller unit 203 produces RF energy which travels via the directional coupler 206, the RF power switch 205, the 180° hybrid power splitter 207 for the case when the RF energy is used to excite a TE type mode in the antenna device 500, coaxial power cables 302 of the interconnection module 300, to either the TE mode feed 516, or the TM mode feed 505 of the antenna device 500. In other embodiments, the 180° hybrid power splitter 207 and the RF power switch 205 can be located in the handpiece 400 or inside the interconnection module 300.

RF detector 1 208, and RF detector 2 209 are used to convert the RF power present on the forward and reflected ports of the directional coupler 206 to voltages which can be read by the controller unit 203. The voltage level at the output of RF detector 1 208 corresponds to the power delivered to the antenna device 500 and thus power dissipated into the patient's tissue. The voltage level at the output of RF detector 2 209 corresponds to the power reflected from the antenna device 500. The measurement by RF detector 2 209 can be used for two purposes: to detect an event where the antenna device 500 is lifted off the patient's skin 601, and to estimate the thickness of the fat layer 602 by sweeping frequency of a low power RF signal around the nominal operating frequency of the antenna device 500 while the latter is configured to operate in quasi TE111 mode. This is possible because the resonant frequency of the antenna device 500 operating in quasi TE111 mode shifts lower if the thickness of the fat layer is increased. A more precise fat thickness estimation can be made by measuring not just the total signal power at the detector 2 209 but also via the magnitude and the phase measurement of this signal.

The RF switch 205 is used to select whether RF energy is being delivered to the antenna's TE mode feed 516 or the TM mode feed 505. The TM mode feed 505 is located on the main axis of the antenna device 500, is naturally axisymmetric and thus only requires a single coaxial cable to be powered. In another embodiment, the TE mode feed 516 can be implemented as a single wire loop requiring a single coaxial cable. In practice, such implementation breaks symmetry of the antenna device and could result in uneven heating pattern in the skin. To address this problem, a preferred embodiment of the antenna device 500 will have a differential TE mode feed 516 driven by two coaxial cables. Yet another embodiment of the antenna device 500 will have two wire loops driven differentially using two coaxial cables.

The RF switch 205 can be put in either a fixed state where the RF energy is used to target either exclusively skin or exclusively fat, or it can be switched back and forth at a relatively high rate (high rate when compared to the thermal constant of the human tissue), for example at a rate of 100 Hz or higher, with the variable duty cycle controlled via the controller unit 203. The latter technique would allow heating of the skin layer 601 and the fat layer 602 simultaneously in a desired proportion.

When operating the antenna device 500 in quasi TM010 mode, which is intended to deliver energy primarily to the subcutaneous fat tissue 602, some unintentional heating of skin 601 will also occur. The skin temperature rise can be calculated via monitoring air temperature flowing above the skin using the plurality of temperature sensors C 517 located at various points within the airduct 512, by reading the airflow meter 211 (and/or airflow meter 212, if implemented), and by measuring the temperature of the antenna device 500 via temperature sensors A 501 and B 502. The flow of cooling air can be dynamically adjusted to keep the skin sufficiently cool. The degree of heating is such that for the embodiment of the antenna device 500 shown in FIGS. 2A and 2B, a gentle airflow of 2 meters per second or higher was shown through simulations to sufficiently cool these skin areas. Therefore, no cryogenic cooling system is required to operate the system 100.

The aircooling is achieved by the air pump 210 creating either positive or negative pressure in the air line 301. This in turn creates positive or negative pressure in the large airduct 402, a number of small air channels 513 which results in the airflow through the ring shaped airduct 512 located at the bottom of the antenna device 500 above the patient's skin 601. In the case of positive pressure, the air from ring shaped airduct 512 is exhausted via a plurality of vent holes 514 linking the ring shaped airduct 512 with ambient air surrounding the antenna device 500. The main advantage of using positive pressure is the ability to reach lower air temperature at the skin surface. As the pressurized air travels through the plurality of small air channels 513 into the ring shaped airduct 512 it undergoes adiabatic expansion and, as a result, the temperature of the cooling air will drop below the temperature of the antenna device 500 thus providing an effective cooling mechanism. The main advantage of using negative pressure for cooling is the ability to create a suction force between the handpiece 400 and the patient's skin 601 and thus providing a mechanism to hold the handpiece 400 in place during treatment. Aircooling mechanism can be improved by utilizing auxiliary airduct 519 and a plurality of venting holes 520 embedded in the temperature sensor A housing 511. In particular, the addition of these aircooling components will allow keeping the epidermis layer at a lower temperature when operating the antenna device 500 in the skin heating mode.

Located inside the handpiece 400 there are a plurality of force sensors 404 used to determine whether the handpiece 400 is making a good connection with the skin 601. The force sensors 404 are connected to the controller unit 203 in the console 200. If it is determined that the handpiece 400 is partly or fully lifted of the patient's skin, the controller unit 203 will disable power delivery to the antenna device 500. According to some embodiments there may be three or more temperature sensors in the handpiece 400, with temperature sensor A 501 located in the center part of the antenna device 500 near the patient's skin, while temperature sensor B 502 is located on the metal body of the antenna device 500, either on the outer surface of the metallic horn 508 or the resonant tank 503. Having at least two temperature sensors allows the calculation of heat flow through the antenna device 500 which is necessary for making accurate temperature measurements of the skin surface 601 and estimating the internal temperature of the fat layer 602. The latter can be achieved by running a sequence of test routines described later in this work.

Referring to FIGS. 2A and 2B, the plurality of controls 403 located on the handpiece 400 are electrically connected to the control unit 203 in the console 200 and can be used by the operator, for instance, to enable or disable RF power delivery, adjust flow of cooling air, and initiate specific test routines, such as estimating fat layer thickness, etc.

A plurality of standoffs 515 located inside the ring shaped airduct 512 that protrude toward the skin ensure that when the antenna device 500 is pressed down against the patient's skin 601, the airflow through the ring shaped airduct 512 is not obstructed.

One important construction detail of the antenna device 500 is the profile of the bottom surface 510. It is optimized to meet the following requirements: the patient's skin 601 can conform easily to the bottom surface 510 of the antenna device 500; the electric field of the quasi TM010 mode is mostly normal to the skin surface within the perimeter of the temperature sensor A housing 511 where the electric fields are most intense. These requirements ensure that any undesirable skin heating is reduced while the intentional heating of fat is increased when the antenna device operates in quasi TM010 mode.

Similarly, the height of the horn 508, the inclination angle of the side wall of the horn 508, and the permittivity of the horn's dielectric fill 509 are optimized to reduce skin heating while intentionally heating fat when the antenna device 500 operates in quasi TM010 mode.

An example of the practical implementation of the antenna device is shown in FIGS. 2A and 2B. The diameter and height of the antenna device 500 are approximately equal to 10 cm, relative permittivity of dielectric material 504 is 6.5, relative permittivity of dielectric material 509 is 9.4, relative permittivity of dielectric material of the temperature sensor A housing 511 is 2.1, approximate diameter of the temperature sensor A housing 511 is 4 cm, the resonant frequency of the antenna device 500 is approximately 915 MHz. According to the simulations, with the skin layer thickness of 0.2 cm and fat layer thickness of 3 cm, the volume of the fat located right below the temperature sensor A housing 511 can be heated to 53° C. in 90 seconds using a 80 Watt power source. At the same time, the skin temperature stays below 47° C. anywhere within the footprint of the antenna device 500, while heating of the muscle tissue is negligible. Conversely, when simulating intentional heating of the skin layer 601, the temperature of skin located within the boundaries of the temperature sensor A housing 511 rises to 50° C. in less than 40 seconds using a 50 Watt power source. There is no measurable heating of fat in this case, with the temperature of underlying muscle rising to approximately 39° C. In another simulated scenario, tissue heating was purposely limited to 45° C., a temperature value which can generally be tolerated without use of anesthetics. In this scenario, fat can be heated to 45° C. in 80 seconds using a 50 Watt power source. At the same time, the skin temperature stays below 41° C. Conversely, when simulating intentional heating of skin, the temperature of skin rises to 45° C. within 20 seconds using a 50 Watt power source. There is no notable heating of fat in this case, with the temperature of underlying muscle rising to approximately 38.5° C.

To administer treatment using the system 100 disclosed herein, the operator places the handpiece 400 on a desired area of patient's body 600. It may be advantageous to moisten the patient's skin 601 prior to application of the handpiece 400. The substance used to moisten the skin should maintain skin moisture for the duration of the treatment cycle. Ideally, the handpiece 400 would be pressed against patient's body 600 by the operator as this ensures most precise placement of the handpiece 400. As an alternative, the handpiece 400 can be secured on patient's body 600 by other means, such as vacuum suction, as previously described.

The operator then initiates a short sequence of test routines via the GUI 202 on the system console 200 to determine the unique skin 601 and fat layer 602 characteristics of the patient undergoing treatment. The tests can include the following:

(i) Applying a low power RF signal to the TE mode feed 516 of the antenna device 500 for short duration to estimate the thickness of the fat layer 602. As previously mentioned, the resonant frequency of the antenna device 500 loaded with skin 601, fat 602 and muscle 603 tissues for TE111-like mode decreases slightly as the thickness of the fat layer 602, and thereby the distance to the muscle layer 603, increases. Thus performing a low power frequency sweep of the loaded antenna device 500 using TE111-like mode can assist with estimating the fat layer 602 thickness and therefore with calculating the optimal amount of energy needed to heat fat to the therapeutic temperature.

(ii) Applying high power RF signal to the TE mode feed 516 of the antenna device 500 for short duration to cause temperature rise in the skin layer 601 and estimate the thermal conductance of the skin layer portion located within the perimeter of the antenna device 500. This is possible since the thermal properties of the dielectric material 509 and the temperature sensor A housing 511 are known by design, the thermal conductivity of the temperature sensor A housing 511 is chosen to be small when compared to that of the skin, and the thermal conductivity of the fat layer 602 is also low when compared to that of the skin; thus the objective can be achieved by monitoring the temperature readings from the temperature sensor A 501 and the temperature sensor B 502 for duration of several seconds after the RF power has been applied to the skin layer 601.

(iii) Applying high power RF signal to the TM mode feed 505 of the antenna device 500 for a short duration to cause a temperature rise in the fat layer 602 and make an additional thickness estimate of the fat layer 602. This can be achieved by monitoring the temperature readings from the temperature sensor A 501 and the temperature sensor B 502 for a duration of several seconds after the RF power has been applied to the fat layer 602, and by using skin layer thermal conductance data measured in the previous test.

Based on the measurements described above and by utilizing modeling data, an estimate can be made for the amount of required energy delivered to the TM mode feed 516 of the antenna device 500 to cause a therapeutic temperature rise of fat.

The dosage of energy delivery to the skin is easily estimated since the skin layer 601 comes in direct contact with the temperature sensor A housing 511; thus the skin surface temperature can be calculated by reading temperature sensor A 501 and the temperature sensor B 502 since thermal properties of the dielectric material 509 and the temperature sensor A housing 511 are known by design.

In some applications it may be important to know the skin temperature as a function of the skin depth. Such knowledge may be used to control the depth of skin at which peak temperatures are attained during treatment. As an example, if subcutaneous fat is heated immediately before treating skin, deeper layers of dermis will reach higher temperature when compared to the case when fat is not heated. For these situations, the skin temperature distribution can be calculated based on the skin layer thermal conductance and fat thickness measurements described above, and through use of thermal modeling.

Having completed execution of the test routines described above and based on the preferred treatment regimen for a given patient, the operator can then set one or more target tissue layers, the order in which they to be treated, the target temperature value in the skin 601 and fat 602 layers and the duration of treatment for each layer. Once the selected location on the patient's body 600 has been treated, the operator will repeatedly relocate the handpiece 400 to a different location on patient's body 600 and reapply treatment until the entire designated area has been treated.

In another embodiment, the system 100 can be a single compact hand-held module used primarily for skin rejuvenation. In this embodiment, the antenna device has an approximate diameter of 1 cm and is coupled to a low power RF energy source; the patient will self-administer treatment at home. Such a system can be battery powered and may not need an air pumping component.

In another embodiment, the handpiece 400 of the system 100 comprises a plurality of light sources emitting light with a blue or violet spectrum. Such sources could be LEDs or laser diodes. The system of this embodiment would be suitable to treat acne by simultaneous application of light and heat to the affected area of the skin.

What is claimed is:

1. An apparatus for providing radio frequency (RF) therapy to a patient, the apparatus comprising:
   a handpiece comprising an antenna device and a contact surface configured for placement in proximity to the patient's skin, wherein
   the antenna device is configured to selectably operate in a first mode in which the antenna device generates only transverse electric (TE) mode RF radiation and in a second mode in which the antenna device generates only transverse magnetic (TM) mode RF radiation having an electric field that is substantially normal with respect to the patient's skin, and
   a switch configured to select between the first mode and the second mode.

2. The apparatus of claim 1, wherein the antenna device is configurable to be operated in the first mode and in the second mode simultaneously.

3. The apparatus of claim 2, wherein the antenna device is configurable to simultaneously generate a first amount of electric field according to the first mode and a second amount of electric field according to the second mode, wherein the first and second amounts of electric field can selectably be the same or different.

4. The apparatus of claim 1, wherein the antenna device comprises a resonator tank, a transverse magnetic mode feed, and a transverse electric mode feed.

5. The apparatus of claim 4, wherein the transverse magnetic mode feed and the transverse electric mode feed are substantially orthogonal to each other.

6. The apparatus of claim 4, wherein the resonator tank contains a dielectric material.

7. The apparatus of claim 6, wherein the dielectric material is a moldable thermoplastic.

8. The apparatus of claim 4, wherein the resonator tank is axisymmetric.

9. The apparatus of claim 4, wherein the handpiece further comprises a horn, wherein the contact surface is integral with the horn.

10. The apparatus of claim 9, wherein the combined height of the resonator tank and horn is approximately equal to the diameter of the resonator tank.

11. The apparatus of claim 1, wherein the handpiece further comprises one or more airducts configured to provide air to the patient's skin.

12. The apparatus of claim 1, wherein the handpiece further comprises one or more temperature sensors.

13. The apparatus of claim 1, wherein the RF radiation has a frequency between 400 MHz and 6 GHz.

14. The apparatus of claim 1, further comprising a console.

15. The apparatus of claim 14, wherein the console comprises a graphical user interface (GUI).

16. The apparatus of claim 14, wherein the console comprises an air pump.

17. The apparatus of claim 14, wherein the console comprises an RF power source coupled to an RF switch and a 180° hybrid power splitter.

18. The apparatus of claim 14, wherein the console comprises one or more RF detectors configured to measure power delivered to the antenna device and power reflected from the antenna device.

19. The apparatus of claim 14, wherein the console comprises a controller configured to adjust a setting of the antenna device based on a parameter sensed by a sensor in the handpiece.

20. The apparatus of claim 19, wherein the parameter relates to temperature.

21. The apparatus of claim 19, wherein the parameter relates to force.

22. A system for providing radio frequency (RF) therapy to a patient, the system comprising:
a handpiece comprising an antenna device and a contact surface configured for placement in proximity to the patient's skin; and
a console; wherein
the antenna device comprises a resonator tank, a transverse magnetic mode feed, and a transverse electric mode feed; and wherein
the console comprises a controller unit configured to cause the antenna device to selectably operate in a first mode in which the antenna device generates only transverse electric (TE) mode RF radiation and in a second mode in which the antenna device generates only transverse magnetic(TM) mode RF radiation having an electric field that is substantially normal with respect to the patient's skin.

23. A method of providing radio frequency (RF) therapy to a patient, the method comprising:
positioning an antenna device in proximity to the patient's skin;
selecting to heat either predominantly a layer of subcutaneous fat of the patient or predominantly the patient's skin;
if the selecting comprises selecting to heat predominantly a layer of subcutaneous fat, causing the antenna device to generate transverse magnetic (TM) mode RF radiation, and
if the selecting comprises selecting to heat predominantly the patient's skin, causing the antenna device to generate transverse electric (TE) mode RF radiation having an electric field that is substantially tangential with respect to the patient's skin.

24. The method of claim 23, further comprising:
using the antenna device to generate TE mode RF radiation;
determining a change in a resonant frequency of the antenna device; and
estimating a thickness of a fat layer of the patient based on the change.

25. The method of claim 23, further comprising:
using the antenna device to generate TE mode RF radiation;
determining a difference in temperature at two positions upon the patient's skin; and
estimating a thermal conductance of the patient's skin based on the difference.

26. The apparatus of claim 23, further comprising:
using the antenna device to generate TM mode RF radiation having an electric field that is substantially normal to the patient's skin;
determining a change in temperature of the patient's skin following application of the RF radiation; and
estimating a thickness of a fat layer of the patient based on the change.

27. The method of claim 23, further comprising sensing a temperature of the patient's skin and ceasing generating the RF radiation if the temperature exceeds a predetermined value.

28. The method of claim 23, further comprising providing cool air to the patient's skin.

29. A method of providing radio frequency (RF) therapy to a patient, the method comprising:
positioning a handpiece in proximity to the patient's skin, wherein the handpiece comprises an antenna device and a contact surface configured for placement in proximity to the patient's skin;
selecting to heat either predominantly a layer of subcutaneous fat of the patient or predominantly the patient's skin;
if the selecting comprises selecting to heat predominantly a layer of subcutaneous fat, causing the antenna device to generate transverse magnetic (TM) mode RF radiation having an electric field that is substantially normal with respect to the patient's skin, and if the selecting comprises selecting to heat predominantly the patient's skin, causing the antenna device to generate transverse electric (TE) mode RF radiation.

30. The method of claim 29, wherein selecting comprises selecting a choice displayed upon a graphical user interface (GUI).

31. The method of claim 30, wherein the GUI is contained within a console operably connected to the handpiece.

* * * * *